United States Patent [19]

Iizuka et al.

[11] Patent Number: 4,469,865

[45] Date of Patent: Sep. 4, 1984

[54] 1,3-DISUBSTITUTED IMIDAZOLES

[75] Inventors: Kinji Iizuka; Tetsuhide Kamijo; Ryoji Yamamoto; Hiromu Harada, all of Nagano, Japan

[73] Assignees: Kissei Pharmaceutical Co., Ltd., Nagano; Ono Pharmaceutical Co., Ltd., Osaka, both of Japan

[21] Appl. No.: 423,332

[22] Filed: Sep. 24, 1982

[30] Foreign Application Priority Data

Sep. 28, 1981 [JP] Japan .................... 56-153404

[51] Int. Cl.$^3$ ................... C07D 233/61; C07D 233/60
[52] U.S. Cl. ................................ 548/341
[58] Field of Search ............... 548/341; 542/400, 458, 542/468, 470

[56] References Cited

FOREIGN PATENT DOCUMENTS 0058079 8/1982 European Pat. Off. ........... 548/335

OTHER PUBLICATIONS

Loozen, H., et al., *J. Org. Chem.*, 40 (22), 3279 (1975).
*Chemical Abstracts*, 86:155649t (1977) [Japan, Kokai No. 76,105,060, 9/17/76].
Godefroi, E., et al., *Rec. Trav. Chim. Pyas–Bas*, 93, 56 (1974).
Olofson, R., et al., *J. Org. Chem.*, 35 (7), 2246 (1970).
Boyer, J., *J. Am. Chem. Soc.*, 74, 6274 (1952).
Staab, H., *Angew. Chem. Internat. Edit.*, 1 (7), 351 (1962).
Birkofer, L., et al., *Chem. Ber.*, 93, 2804 (1960).
Curtis, N., *J. Org. Chem.*, 45, 4038 (1980).
Van Der Eijk, J., et al., *J. Org. Chem.*, 45, 547 (1980).
Kamijo, T., et al., *Chem. Pharm. Bull. Japan*, 31 (4), 1213 (1983).
Iizuka, K., et al., *J. Med. Chem.*, 24, 1139 (1981).
Grimmett, M., *Adv. Heterocycl. Chem.* 12, 103 (1970).
Haring, M., *Helv. Chim. Acta.*, XLII, 1845 (1959).
Baggaley, K., et al., *J. Med. Chem.*, 18 (8), 833 (1975).
Walker, K., et al., *J. Med. Chem.*, 24 (1), 67 (1981).
Nardi, D., et al., *J. Med. Chem.*, 24 (6), 727 (1981).
Godefroi, E., et al., *J. Med. Chem.*, 12, 784 (1969).
Kikugawa, Y., *Synthesis*, 124 (1981).
Yamauchi, K., *J.C.S. Perkin I*, 1973, 2506.
Mcomie, J., (Editor), *Protective Groups in Organic Chemistry*, Plenum Press, London, 1973, pp. 46 and 49.

*Primary Examiner*—Richard A. Schwartz
*Attorney, Agent, or Firm*—Sughrue, Mion, Zinn, Macpeak, and Seas

[57] ABSTRACT

1,3-Disubstituted imidazoles of the general formula (I):

$$Y-N\underset{(+)}{\overset{\frown}{\underset{\smile}{\bigcirc}}}N-A-\bigcirc-(B)_n-Z \quad X^- \quad (I)$$

wherein A and B may be the same or different, and each is a straight- or branched-chain alkylene or alkenylene group having 1 to 8 carbon atoms, Y is an acyl group having 2 to 10 carbon atoms, an alkoxycarbonyl group having 2 to 7 carbon atoms or an dialkoxymethyl group having 3 to 13 carbon atoms, Z is a cyano group or an alkoxycarbonyl group having 2 to 7 carbon atoms, X is a halogen atom, n is zero or 1. The said compounds are intermediates for producing the imidazole derivatives of the general formula (V) above which possess strong and specific inhibitory effects on thromboxane synthetase and thus are useful as therapeutical agents for treatment of diseases caused by thromboxane $A_2$.

24 Claims, No Drawings

1,3-DISUBSTITUTED IMIDAZOLES

FIELD OF THE INVENTION

This invention relates to novel imidazole derivatives and to a process for their preparation. More particularly, this invention relates to 1,3-disubstituted imidazoles being useful as intermediates in producing N-(ω-substituted alkylphenylalkyl) and N-(nuclear substituted phenylalkyl)-imidazoles of the general formula (I) below which exhibit strong and specific inhibitory effects on thromboxane synthetase and thus are useful as therapeutically active agents for treatment of diseases caused by thromboxane $A_2$.

BACKGROUND OF THE INVENTION

The imidazole derivatives of the general formula (V):

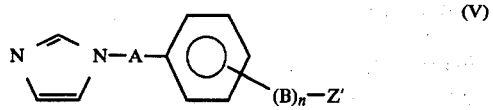

wherein A and B may be the same or different, and each is a straight- or branched-chain alkylene or alkenylene group having 1 to 8 carbon atoms, Z' is a carboxyl group or an alkoxycarbonyl group, n is zero or 1; especially compounds wherein the aggregate number of linear carbon atoms in A and B in the general formula (V) is 2, 3 or 4 are known to exhibit strong and specific inhibitory effects on thromboxane synthetase and thus are useful as therapeutical agents for treatment of diseases caused by thromboxane $A_2$, as reported in U.S. Pat. No. 4,226,878. Furthermore, several methods for producing said derivatives have been also disclosed in the above U.S. patent.

All the methods disclosed in said British patent application comprises a process of N-alkylating reaction of an imidazole with a halide in the procedure of synthesis of said imidazole derivatives, and therefore, there is a problem in these conventional methods that di-N-alkylation can occur and an imidazolium compound is produced as a by-product in a large amount. Such by-product adversely affects the yield and purity of the desired product.

Accordingly, it is an object of this invention to provide 1,3-disubstituted imidazoles having the general formula (I) below which are useful as intermediates in the production of the imidazole derivatives of the general formula (V) above.

It is another object of this invention to provide a process for producing 1,3-disubstituted imidazoles (I) below.

It is still another object of this invention to provide a new process for producing the imidazole derivatives of the general formula (V) above, which is superior to prior art methods such as those described in the above U.S. patent.

Other objects and advantages of this invention will become apparent from the following description and examples.

DESCRIPTION OF THE INVENTION

This invention provides 1,3-disubstituted imidazoles of the general formula (I):

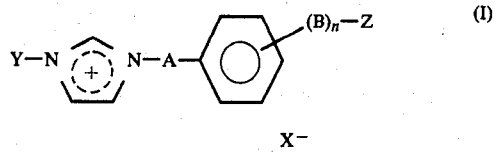

wherein A and B may be the same or different, and each is a straight- or branched-chain alkylene or alkenylene group having 1 to 8 carbon atoms, Y is an acyl group having 2 to 10 carbon atoms, an alkoxycarbonyl group having 2 to 7 carbon atoms or an dialkoxymethyl group having 3 to 13 carbon atoms, Z is a cyano group or an alkoxycarbonyl group having 2 to 7 carbon atoms, X is a halogen atom, n is zero or 1. The said compounds are intermediates for producing the imidazole derivatives of the general formula (V) above which possess strong and specific inhibitory effects on thromboxane synthetase and thus are useful as therapeutical agents for treatment of diseases caused by thromboxane $A_2$.

The compound of the general formula (I) of this invention can be prepared by reacting a 1-substituted imidazole of the general formula (II):

wherein Y is as previously defined, with a halide of the general formula (III):

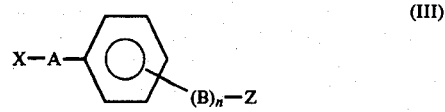

wherein X, A, Z, B and n are as previously defined.

The compounds corresponding to the general formula (II) which are employed as starting materials are known compounds, and can be prepared according to the methods of synthesis described in chemical literatures such as J. Amer. Chem. Soc. 74, 6274 (1952), J. Org. Chem. 45, 4038 (1980), Angew. Chem. Int. Ed. Engl. 1, 351 (1962), Chem. Ber. 93, 2804 (1960). Examples of said compounds include 1-acetylimidazole, 1-propionylimidazole, 1-benzoylimidazole, 1-(4-methylbenzoyl)-imidazole, 1-(4-methoxybenzoyl)imidazole, 1-ethoxycarbonyl-imidazole, 1-diethoxymethylimidazole. Preferred compounds are 1-acetylimidazole and 1-benzoylimidazole, and the most preferred compound is 1-acetylimidazole.

The compounds of the general formula (III) used as starting material are generally known compounds, and can be prepared according to the methods described in chemical literatures such as J. Chem. Soc. 1942, 103, Chem. Abstr. 60, 10707c (1964) Chem. Abstr. 62, 159 1h (1965), Chem. Abstr. 64, 17737b (1966), J. Pharm. Sci. 55(3), 295–302 (1966), and J. Org. Chem. 35(9), 3161–4 (1970). Examples of said compounds include alkyl esters having 1 to 6 carbon atoms of 2-, 3- or 4-chlorobenzoic acid, 2-, 3- or 4- bromomethylbenzoic acid, 2-, 3- or 4-iodomethylbenzoic acid, 2-, 3- or 4-chloromethylcinnamic acid, 2-, 3- or 4-bromomethylcinnamic acid, 2-, 3- or 4-iodomethylcinnamic acid, 3-(2-, 3- or 4-chloromethylphenyl)propionic acid, 3-(2-, 3- or 4- bromomethylphenyl)propionic acid, 3-(2-, 3- or 4-iodomethyl-phenyl)propionic acid, 4-(2-, 3- or 4-chloromethylphenyl)- butyric acid, 4-(2-, 3- or 4-bromomethylphenyl)butyric acid, 4-(2, 3- or 4-iodomethylphenyl)butyric acid, 2-, 3- or 4-chloromethyl-α-methylcinnamic acid, 2-, 3- or 4-bromomethyl-α-methylcinnamic acid, 2-, 3- or 4-iodomethyl-α-methylcinnamic acid, 2-, 3- or 4-(2-bromoethyl)benzoic acid, 2-, 3- or 4-(2--iodoethyl)benzoic acid, 2-, 3- or 4-(2-bromoethyl)- phenylacetic acid, 2-, 3- or 4-(2-iodoethyl)phenylacetic acid, 2-, 3- or 4-(3-bromopropyl)benzoic acid, 2-, 3- or 4-(3-iodopropyl)benzoic acid, 2-, 3- or 4-(3-bromo-1-propenyl)- benzoic acid, 2-, 3- or 4-(3-iodo-1-propenyl)benzoic acid and the like, and the corresponding nitriles of the above ester compounds.

The compounds of the general formula (I) of this invention can be easily prepared by the following procedure: A 1-substituted imidazole of the general formula (II) is treated with a halide of the general formula (III) for from about 30 minutes to overnight (about 10–20 hours) at from room temperature (about 20°–30° C.) to about 150° C. under stirring in the absence of or in the presence of an inert organic solvent such as chloroform, methylene chloride, benzene, toluene, acetonitrile, preferably acetonitrile. After completion of the reaction, an adequate amount of an organic solvent such as diethyl ether is added to the reaction mixture or, if necessary, to the residue obtained after evaporating the reaction mixture, and the precipitated crystals or crystalline powders are collected by filtration and dried to give the desired compound of the general formula (I), if optionally, with recrystallization using an adequate organic solvent.

The 1,3-disubstituted imidazoles of the general formula (I) of this invention are novel compounds not previously disclosed in literatures. Examples of the compounds of the general formula (I) include 1-acetyl-3-[2-(2-ethoxycarbonyl- vinyl)benzyl]imidazolium bromide, 1-acetyl-3-[3-(2-ethoxy- carbonylvinyl)benzyl]imidazolium bromide, 1-acetyl-3-[4-(2-methoxycarbonylvinyl)benzyl]imidazolium bromide, 1-acetyl-3-[4-(2-ethoxycarbonyl-1-propenyl)benzyl]imidazolium iodide, 1-acetyl-3--[4-(2-cyanovinyl)benzyl]imidazolium bromide, 1-acetyl-3-[4-(2-ethoxycarbonylethyl)benzyl]imidazolium iodide, 1-acetyl-3-[3-(4-ethoxycarbonylphenyl)propyl]- imidazolium iodide, 1-acetyl-3-(4-ethoxycarbonylcinnamyl)- imidazolium bromide, 1-benzoyl-3-[4-(2-methoxycarbonylvinyl)- benzyl]imidazolium bromide, 1-benzoyl-3-[4-(2-ethoxycarbonyl-1-propenyl)benzyl]imidazolium iodide, 1-ethoxycarbonyl-3-[4-(2-methoxycarbonylvinyl)benzyl]imidazolium bromide and the like.

Of these compounds of the general formula (I) above, compounds wherein the aggregate number of linear carbon atoms in A and B in the general formula (I) is 2, 3 or 4 are preferable in this invention.

In accordance with the present invention process, the problem associated with the procedures disclosed in the above U.S. patent, i.e. formation of an imidazolium compound as a by-product, is eliminated, therefore, according to the prior art methods such as those disclosed in U.S. Pat. No. 4,226,873, N-alkylating reaction of imidazole with a halide can be carried out by using imidaozle in an excess amount to the halide in order to reduce the production of a by-product such as an imidazolium compound. However, in the invention process, it is not necessary to employ 1-substituted imidazoles of the general formula (II) above in an excess amount to halides of the general formula (III) above and the desired products can be obtained in a good yield with high purity by using an equimolar amount of 1-substituted imidazoles of the general formula (II) and halides of the general formula (III) above. Thus the 1-substituted imidazoles of the general formula (II) used as starting materials can be employed efficiently.

Furthermore, as the reaction can be carried out under a neutral condition and the reaction condition is mild, the formation of by-products is little and the desired product (I) can be obtained in a good yield with high purity.

The 1,3-disubstituted imidazoles of the general formula (I) of this invention can be easily converted in good yield into the imdazole derivatives of the general formula (V). That is, the imidazole derivatives of the general formula (V) can be obtained by treating an aqueous solution of the 1,3-disubstituted imidazoles of the general formula (I) at from room temperature to 120° C. for from 10 minutes to 3 hours with an acidic or a basic compound, for example, inorganic acid such as hydrochloric acid, hydrobromic acid, sulfuric acid, phosphoric acid and the like, or organic and inorganic base such as sodium hydroxide, potassium hydroxide, sodium carbonate, potassium carbonate, sodium bicarbonate, potassium bicarbonate, methylamine, ethylamine, dimethylamine, diethylamine, trimethylamine, triethylamine, piperidine, pyrrolidine, morpholine and the like.

Thus, in accordance with the process of this invention, as a further advantage, the imidazole derivatives of the general formula (V) above, can be easily obtained in a high yield and purity at a low cost compared with the prior art methods disclosed in the above U.S. Pat. No. 4,226,878.

Accordingly, the 1,3-disubstituted imidazoles of the general formula (I) of this invention are important intermediates for producing the imidazole derivatives of the general formula (V) above which possess strong and specific inhibitory effects on thromboxane synthetase and thus are useful as therapeutical agents for treatment of diseases caused by thromboxane $A_2$, and the process of this invention is advantageous in the production of the imidazole derivatives of the general formula (V) above on an industrial scale, which is superior to prior art methods such as these described in the U.S. Pat. No. 4,226,878.

This invention is further illustrated in more detail by the following examples wherein the melting point of the product obtained is uncorrected.

EXAMPLE I

To 7.0 ml of dry acetonitrile were added 1.43 g of 1-acetyimidazole and 3.33 g of methyl 4-bromomethylcinnamate, and the mixture was stirred overnight at room temperature. The precipitated crystals were collected by filtration and recrystallized from acetonitrile/diethyl ether to yield 4.75 g of 1-acetyl-3-[4-(2-methoxycarbonylvinyl)benzyl]imidazolium bromide.

Melting Point: 153°–154° C.
IR-absorption spectra (KBr):
$\nu$CO: 1770 cm$^{-1}$, 1715 cm$^{-1}$.
NMR spectra (d$_6$-DMSO):
$\delta$: 1.90(s, 3H), 3.75(s, 3H), 5.50(s, 2H), 6.67(d, 1H, J=16Hz), 7.36–7.90(m, 7H), 9.31(m, 1H).
Elementary analysis as $C_{16}H_{17}O_3N_2Br$:

|  | C % | H % | N % |
|---|---|---|---|
| Calcd. | 52.61 | 4.69 | 7.67 |
| Found | 52.80 | 4.60 | 7.83 |

EXAMPLE 2

To 5 ml of dry acetonitrile were added 1.7 g of 1-benzoylimidazole and 2.6 g of methyl 4-bromomethylcinnamate, and the mixture was stirred for 5 hours at room temperature. The precipitated crystals were collected by filtration and recrystallized from acetonitrile/diethyl ether to yield 3.5 g of 1-benzoyl-3-[4-(2-methoxycarbonylvinyl)benzyl]imidazolium bromide.

Melting Point: 154°–156° C.
IR-absorption spectra (KBr)
$\nu$CO: 1785 cm$^{-1}$, 1745 cm$^{-1}$, 1720 cm$^{-1}$.
NMR spectra (d$_6$-DMSO):
δ: 3.72(s, 2H), 5.50(s, 3H), 6.66(d, 1H), J=16 Hz), 7.33–8.07(m, 12H), 9.36(m, 1H).
Elementary analysis as $C_{21}H_{19}O_3N_2Br$:

|  | C % | H % | N % |
|---|---|---|---|
| Calcd. | 59.02 | 4.48 | 6.56 |
| Found | 59.03 | 4.46 | 6.55 |

EXAMPLE 3

To 5 ml of dry acetonitrile were added 1.4 g of 1-ethoxycarbonylimidazole and 2.55 g of methyl 4-bromomethylcinnamate, the mixture was stirred for 5 hours at room temperature. The precipitated crystals were collected by filtration and recrystallized from acetonitrile/diethyl ether to yield 2.9 g of 1-ethoxycarbonyl-3-[4-(2-methoxycarbonylvinyl)benzyl]imidazolium bromide.

Melting Point: 129° C. (decomposition).
IR-absorption spectra (KBr):
$\nu$CO: 1785 cm$^{-1}$, 1715 cm$^{-1}$.
NMR spectra (d$_6$-DMSO):
δ: 1.35(t, 3H, J=7 Hz), 3.70(s, 3H), 4.53(q, 2H, J=7 Hz), 5.60(s, 2H), 7.47–8.00(m, 5H), 8.10(m, 1H), 8.25(m, 1H), 8.65(d, 1H, J=16 Hz), 10.27(m, 1H).
Elementary analysis as $C_{17}H_{19}O_4N_2Br$:

|  | C % | H % | N % |
|---|---|---|---|
| Calcd. | 51.66 | 4.85 | 7.09 |
| Found | 51.64 | 4.93 | 7.12 |

EXAMPLE 4

To 10 ml of dry acetonitrile were added 3.3 g of 1-acetylimidazole and 8.04 g of 4-ethoxycarbonylcinnamyl bromide, and the mixture was heated for 3 hours at 60° C. under stirring. After cooling, to the reaction mixture was added an adequate amount of dry diethyl ether and the resulting powder was collected by filtration and dried to obtain 10.8 g of 1-acetyl-3-(4-ethoxycarbonylcinnamyl)-imidazolium bromide. (colorless hygroscopic amorphous).

IR-absorption spectra (KBr): $\nu$CO: 1775 cm$^{-1}$, 1715 cm$^{-1}$.
NMR spectra (d$_6$-DMSO):
δ: 1.31(t, 3H, J=7 Hz), 1.90(s, 3H), 4.33(q, 2H, J=7 Hz), 5.13(d, 2H, J=5 Hz), 6.67–6.85 (m, 2H), 7.65(d, 2H, J=8 Hz), 7.78(m, 1H), 7.87(m, 1H), 7.95(d, 2H, J=8 Hz), 9.27(m, 1H).

EXAMPLE 5

To 10 ml of dry acetonitrile were added 1.1 g of 1-acetylimidazole, 2.26 g of ethyl 4-(3-chloropropyl)benzoate and 1.5 g of sodium iodide, and the mixture was heated in a sealed tube for 18 hours at 140° C. under stirring. After cooling, the reaction mixture was filtrated to remove insoluble materials and the filtrate was concentrated under reduced pressure. To the residue was added an adequate amount of dry diethyl ether and the resulting powder was collected by filtration to obtain 3.99 g of 1-acetyl-3-[3-(4-ethoxycarbonylphenyl)propyl]imidazolium iodide. (pale yellow hygroscopic amorphous).

IR-absorption spectra (KBr): $\nu$CO: 1780 cm$^{-1}$, 1705 cm$^{-1}$.
NMR spectra (d$_6$-DMSO):
δ: 1.33(t, 3H, J=7 Hz), 1.95(s, 3H), 2.00–2.45(m, 2H), 2.60–2.90(m, 2H), 4.05–4.45(m, 2H), 4.35(q, 2H, J=7 Hz), 7.35(m, 1H),
7.40(d, 2H, J=9 Hz), 7.58(m, 1H), 7.93(d, 2H, J=9 Hz), 8.49(m, 1H).

EXAMPLE 6

By using the same procedure as described in Example 1 to Example 5, the following compounds were obtained.

(1)

1-acetyl-3-[2-(2-ethoxycarbonylvinyl)benzyl]imidazolium bromide. (colorless hygroscopic amorphous)

IR-absorption spectra (KBr):
$\nu$CO: 1770 cm$^{-1}$, 1725 cm$^{-1}$.
NMR spectra (d$_6$-DMSO):
δ: 1.25(t, 3H, J=7 Hz), 1.87(s, 3H), 4.20(q, 2H, J=7 Hz), 5.75(s, 2H), 6.50(d, 1H, J=15 Hz), 7.90(d, 1H, J=15 Hz), 7.10–7.95(m, 6H), 9.24(m, 1H).

(2)

1-acetyl-3-[3-(2-ethoxycarbonylvinyl)benzyl]imidazolium bromide. (colorless needles)

Melting Point: 159°–161° C. (recrystal solvent: acetonitrile).
IR-absorption spectra (KBr):
$\nu$CO: 1765 cm$^{-1}$, 1715 cm$^{-1}$.
NMR spectra (d$_6$-DMSO):
δ: 1.22(t, 3H, J=7 Hz), 1.91(s, 3H), 4.20(q, 2H, J=7 Hz), 5.47(s, 2H), 6.68(d, 2H, J=16 Hz), 7.32–8.00(m, 7H), 9.04(m, 1H).

(3) 1-acetyl-3-[4-(2-cyanovinyl)benzyl]imidazolium bromide. (colorless needles)

Melting Point: 147°–150° C. (recrystal solvent: acetonitrile).
IR-absorption spectra (KBr):
$\nu$CO: 1765 cm$^{-1}$
$\nu$CN: 2220 cm$^{-1}$.
NMR spectra (d$_6$-DMSO):
δ: 1.92(s, 3H), 5.55(s, 2H), 6.52(d, 2H, J=16 Hz), 7.40–7.95(m, 7H), 9.37(m, 1H).

(4)
1-acetyl-3-[4-(2-ethoxycarbonyl-1-propenyl)benzyl]-
imidazolium iodide. (colorless needles)

Melting Point: 120°–122° C. (recrystal solvent: acetonitrile).
IR-absorption spectra (KBr):
νCO: 1770 cm⁻¹, 1710 cm⁻¹.
NMR spectra (d₆-DMSO):
δ: 1.30(t, 3H, J=7 Hz), 1.92(s, 3H), 2.05(d, 3H, J=1.5 Hz), 4.22(q, 2H, J=7 Hz), 5.34(s, 2H), 7.12–7.68(m, 7H), 8.36(m, 1H).

(5)
1-acetyl-3-[4-(2-ethoxycarbonylethyl)benzyl-]imidazolium iodide. (colorless hygroscopic amorphous)

IR-absorption spectra (neat):
νCO: 1770 cm⁻¹, 1730 cm⁻¹.
NMR spectra (d₆-DMSO):
δ: 1.14(t, 3H, J=7 Hz), 1.93(s, 3H), 2.55–2.75(m, 2H), 2.75–3.00(m, 2H), 4.07(q, 2H, J=7 Hz), 5.28(s, 2H), 7.25(s, 4H), 7.41(m, 1H), 8.25–8.50(m, 2H).

(6)
1-benzoyl-3-[4-(2-ethoxycarbonyl-1-propenyl)benzyl]-imidazolium iodide. (pale yellow hygroscopic amorphous)

IR-absorption spectra (KBr):
νCO: 1785 cm⁻¹, 1740 cm⁻¹, 1700 cm⁻¹.
NMR spectra (d₆-DMSO):
δ: 1.25(t, 3H, J=7 Hz), 2.03(d, 3H, J=1.5 Hz), 4.20(q, 2H, J=7 Hz), 5.30(s, 2H), 7.00–8.30(m, 13H).

REFERENCE EXAMPLE 1

In 60 ml of 2n hydrochloric acid were dissolved 600 mg of 1-acetyl-3-[4-(2-methoxycarbonylvinyl)benzyl]-imidazolium bromide, and the solution was heated at 80° C. for 1 hour. After completion of the reaction, the solution was concentrated under reduced pressure and to the residue was added an adequate amount of acetone. The precipitated crystals were collected by filtration and dried to yield 450 mg of 4-(1- imidazolylmethyl)cinnamic acid hydrochloride monohydrate.

Melting Point: 228°–232° C. (decomposition).
IR-absorption spectra (KBr):
νCO: 1690 cm⁻¹, 1630 cm⁻¹.
NMR spectra (d₆-DMSO):
δ: 5.55(s, 2H), 6.57(d, 1H, J=16 Hz), 7.40–7.95(m, 7H), 9.44(m, 1H).
Elementary analysis as $C_{13}H_{15}O_3N_2CL$:

|  | C % | H % | N % |
|---|---|---|---|
| Calcd. | 55.22 | 5.35 | 9.91 |
| Found | 55.31 | 5.38 | 9.85 |

REFERENCE EXAMPLE 2

In 30 ml of water were dissolved 3.65 g of 1-acetyl-3-[4-(2-methoxycarbonylvinyl)benzyl]imidazolium bromide and then sodium carbonate was added to make the solution weakly basic. The precipitated crystals were collected by filtration and recrystallized from tetrachloromethane to yield 2.3 g of methyl 4-(1-imidazolylmethyl)cinnamate.

Melting Point: 116°–117° C.

IR-absorption spectra (KBr):
νCO: 1705 cm⁻¹.
NMR spectra (CDCL₃):
δ: 3.80(s, 3H), 5.13(s, 2H), 6.40(d, 1H, J=16 Hz), 6.90(m, 1H), 7.05–7.80(m, 7H).
Elementary analysis as $C_{14}H_{14}O_2N_2$:

|  | C % | H % | N % |
|---|---|---|---|
| Calcd. | 69.40 | 5.82 | 11.56 |
| Found | 69.13 | 5.84 | 11.35 |

What is claimed is:
1. A 1,3-disubstituted imidazole of the following formula:

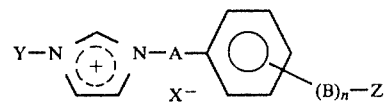

wherein A and B may be the same or different, and each is a straight- or branched-chain alkylene or alkenylene group having 1 to 8 carbon atoms, Y is an acyl group having 2 to 10 carbon atoms, an alkoxycarbonyl group having 2 to 7 carbon atoms or a dialkoxymethyl group having 3 to 13 carbon atoms, Z is a cyano group or an alkoxycarbonyl group having 2 to 7 carbon atoms, X is a halogen atom, n is zero or 1.

2. A 1,3-disubstituted imidazole as claimed in claim 1 wherein said compound has the following formula:

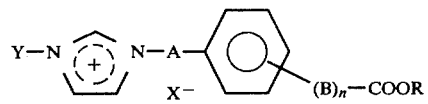

wherein R is an alkyl group having 1 to 6 carbon atoms, Y, A, B X and n are as previously defined.

3. A 1,3-disubstituted imidazole as claimed in claim 2 wherein Y is an acyl group having 2 to 10 carbon atoms.

4. A 1,3-disubstituted imidazole as claimed in claim 3 wherein Y is an acetyl group.

5. A 1,3-disubstituted imidazole as claimed in claim 3 wherein Y is a benzoyl group.

6. A 1,3-disubstituted imidazole as claimed in claim 2 wherein Y is an alkoxycarbonyl group having 2 to 7 carbon atoms.

7. A 1,3-disubstituted imidazole as claimed in claim 6 wherein Y is an ethoxycarbonyl group.

8. A 1,3-disubstituted imidazole as claimed in claim 1 wherein said 1,3-disubstituted imidazole has the following formula:

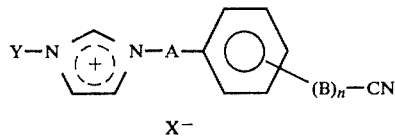

wherein Y, A, B, X and n are previously defined.

9. A 1,3-disubstituted imidazole as claimed in claim 8 wherein Y is an acyl group having 2 to 10 carbon atoms.

10. A 1,3-disubstituted imidazole as claimed in claim 9 wherein Y is an acetyl group.

11. A 1,3-disubstituted imidazole as claimed in claim 9 wherein Y is a benzoyl group.

12. A 1,3-disubstituted imidazole as claimed in claim 8 wherein Y is an alkoxycarbonyl group having 2 to 7 carbon atoms.

13. A 1,3-disubstituted imidazole as claimed in claim 12 wherein Y is an ethoxycarbonyl group.

14. The 1,3-disubstituted imidazole as claimed in claim 4 of the formula:

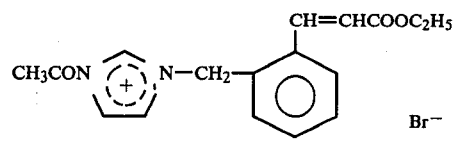

15. The 1,3-disubstituted imidazole as claimed in claim 4 of the formula:

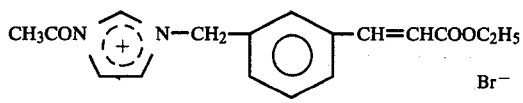

16. The 1,3-disubstituted imidazole as claimed in claim 4 of the formula:

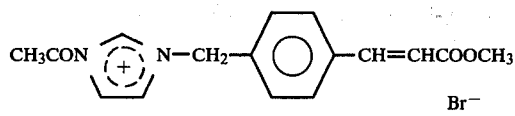

17. The 1,3-disubstituted imidazole as claimed in claim 4 of the formula:

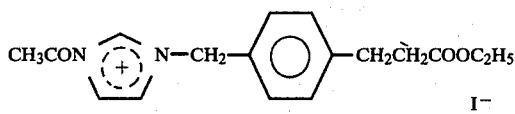

18. The 1,3-disubstituted imidazole as claimed in claim 4 of the formula:

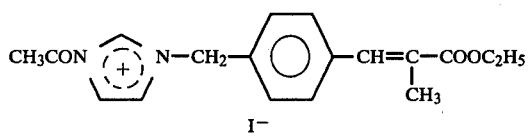

19. The 1,3-disubstituted imidazole as claimed in claim 4 of the formula:

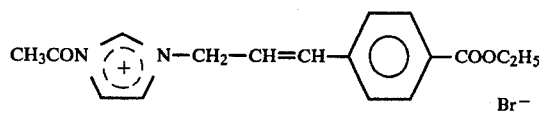

20. The 1,3-disubstituted imidazole as claimed in claim 4 of the formula:

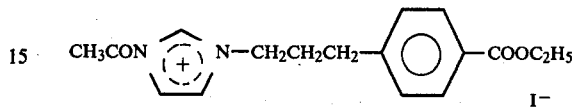

21. The 1,3-disubstituted imidazole as claimed in claim 5 of the formula:

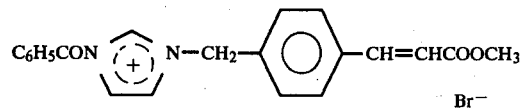

22. The 1,3-disubstituted imidazole as claimed in claim 5 of the formula:

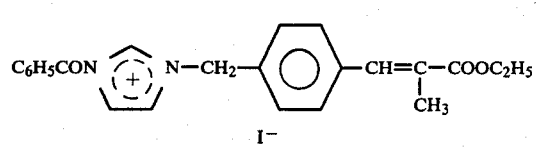

23. The 1,3-disubstituted imidazole as claimed in claim 7 of the formula:

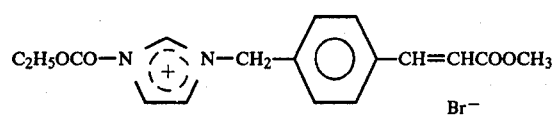

24. The 1,3-disubstituted imidazole as claimed in claim 10 of the formula:

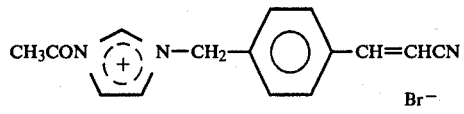

* * * * *